US006432395B1

(12) United States Patent
Rochon et al.

(10) Patent No.: US 6,432,395 B1
(45) Date of Patent: Aug. 13, 2002

(54) CLEANING COMPOSITION CONTAINING NATURALLY-DERIVED COMPONENTS

(75) Inventors: Michael R. Rochon, Caledon; Bernardus M. Tangelder, London, both of (CA)

(73) Assignee: Cogent Environmental Solutions Ltd., Caledon (CA)

( * ) Notice: Subject to any disclaimer, the term of this patent is extended or adjusted under 35 U.S.C. 154(b) by 0 days.

(21) Appl. No.: 09/699,654

(22) Filed: Oct. 30, 2000

Related U.S. Application Data

(60) Provisional application No. 60/163,617, filed on Nov. 4, 1999.

(51) Int. Cl.[7] .......................... A61K 7/075; A61K 7/08; A61K 7/50; A61K 31/56; C09K 3/22
(52) U.S. Cl. .............................. 424/70.19; 424/70.24; 510/135; 510/180; 510/214
(58) Field of Search ................. 510/135, 180, 510/214; 424/70.19, 70.24

(56) References Cited

U.S. PATENT DOCUMENTS

| | | | |
|---|---|---|---|
| 3,793,221 A | 2/1974 | Otrhalek et al. | ............. 252/136 |
| 4,536,317 A | 8/1985 | Llenado et al. | ........ 252/174.17 |
| 4,683,074 A | 7/1987 | Malik et al. | ................. 252/136 |
| 4,687,592 A | 8/1987 | Collins et al. | ................. 252/99 |
| 4,797,481 A | 1/1989 | Garlisi et al. | ............... 536/110 |
| 4,834,903 A | 5/1989 | Roth et al. | ............. 252/174.17 |
| 5,397,397 A | 3/1995 | Awad | ............................. 134/1 |
| 5,540,855 A | 7/1996 | Baillely et al. | ............. 510/276 |
| 5,599,476 A | 2/1997 | Behler et al. | ................ 510/135 |
| 5,653,970 A * | 8/1997 | Vermeer | .................. 424/70.24 |
| 5,683,972 A | 11/1997 | Zocchi | ........................ 510/135 |
| 5,750,489 A | 5/1998 | Garcia et al. | ............... 510/417 |
| 5,753,606 A | 5/1998 | Hess et al. | ................... 510/422 |
| 5,756,438 A | 5/1998 | Rau et al. | .................... 510/151 |
| 5,849,095 A | 12/1998 | Rouilard | ........................ 134/3 |
| 5,932,023 A | 8/1999 | Ward et al. | ..................... 134/3 |
| 5,942,238 A | 8/1999 | McAtee et al. | ................. 424/49 |
| 5,952,275 A | 9/1999 | Feferman et al. | ........... 510/310 |
| 5,981,452 A | 11/1999 | Schrader et al. | ............. 510/155 |
| 5,994,290 A | 11/1999 | Potthoff-Karl et al. | |

OTHER PUBLICATIONS

Pilot Chemical Company, Santa Fe Springs, California, "Personal Care, Eucarol Alkyl Glucoesters" Product Data Sheets, Dated prior to Oct. 4, 1999, 3 unnumbered pages (for convenience, numbered 1, 2, 3) and pp. 8–18.

K. Hill, W. von Rybinski, G. Stoll, "Alkyl Polyglycosides: Technology, Properties and Applications", VCH Verlagsgesellschaft mbH, D–69451 Weinheim (Fed. Rep. of Germany) 1997, Chapters 1, 5, 6 and 13.

* cited by examiner

*Primary Examiner*—Theodore J. Criares
(74) *Attorney, Agent, or Firm*—Pearne & Gordon LLP

(57) ABSTRACT

A less irritating cleaning composition is provided containing only naturally derived components. The composition preferably comprises lactic acid or other C2–C6 organic acid, alkyl polyglucoside, alkyl glucoester and collagen protein.

45 Claims, No Drawings

CLEANING COMPOSITION CONTAINING NATURALLY-DERIVED COMPONENTS

This application claims the benefit of U.S. Provisional Patent Application Ser. No. 60/163,617 filed Nov. 4, 1999.

BACKGROUND OF THE INVENTION

The present invention relates generally to cleaning products, and more particularly, to cleaning products comprising only naturally derived components that exhibit low skin irritancy and rapid environmental degradability. It is known that many people experience a high degree of skin toxicity toward synthetic cleaning products, with problematic results. Many individuals suffer from chronic or acute skin irritation due to an unsanitary home environment, because such individuals must refrain from using commonly available synthetic household cleaners for fear of residual skin irritation. In addition, synthetically derived cleaning products, though somewhat environmentally degradable, are known to persist under certain conditions and are suspected of inducing negative biologic responses in the environment.

Some cleaning product formulations comprising naturally derived components have been developed in response to the above. However, existing natural cleaning products have met with minimal acceptance in the marketplace due to recognized poor cleansing, and similar levels of skin irritancy compared with synthetically derived cleaning products.

Consequently, there is a need in the art for a cleaning product formulation comprising natural components that exhibits excellent cleansing, low skin toxicity, and high environmental degradability or biodegradability. Such a cleaner must further provide a desired foam level and stability, hard water tolerance and rinsing capability. The invented cleaning composition can be used for glass and window cleaners, dishwashing and floor care products and cleaners, food industry cleaners, laundry and carpet cleaners, bathroom cleaners, dairy cleaners, general purpose and industrial cleaners, hard surface cleaners, metal cleaners, as well as transportation products.

SUMMARY OF THE INVENTION

An aqueous cleaning composition is provided comprising 0.004–28 weight percent naturally derived organic acid, 0.0035–36 weight percent naturally derived nonionic surfactant, and 0.0003–7 weight percent naturally derived anionic surfactant.

DETAILED DESCRIPTION OF THE PREFERRED EMBODIMENTS OF THE INVENTION

In the description that follows, when a preferred range, such as 5 to 25 (or 5–25), is given, this means preferably at least 5, and separately and independently, preferably not more than 25. When a range is given in terms of a weight percent (wt. %) for a single component of a composite mixture, this means that the single component is present by weight in the composite mixture in the stated proportion relative to the sum total weight of all components of the composite mixture.

In the preferred embodiments the cleaning formulation of the present invention contains only naturally derived components and is thus free from the presence of non-naturally-derived components. As used herein, "naturally derived" means that a component is obtained or derived solely from naturally occurring, or naturally regenerable resources, in contrast with synthetic components which are artificially synthesized. For example, the surfactant used in the present invention are wholly derived from natural sugars and corn oil, and are termed "naturally derived" because both sugars and corn oil are seasonably regenerable resources. The preferred components (including branded or trademarked components) described or suggested in this patent application are all within the definition of "naturally derived".

The cleaner of the present invention comprises three principal components: an organic acid, an anionic surfactant, and a nonionic surfactant. The organic acid is preferably C1–C20, more preferably C2–C12, more preferably C2–C8, more preferably C2–C6, preferably non-fatty, preferably carboxylic, dicarboxylic and tricarboxylic acid, preferably lactic acid. Less preferably, other naturally derived organic acids, such as malic, citric, maleic, succinic, gluconic, and polyaspartic acids, less preferably other naturally derived organic acids, may be used. Lactic acid is preferred because of its superior ability to solubilize calcium carbonate and other hard water salts compared with other naturally derived acids. The lactic acid also solubilizes rust stains and serves as a preservative for the surfactant components as explained below.

The anionic surfactant component may be a single naturally derived surfactant or a combination of multiple naturally derived anionic surfactants. The preferred anionic surfactant is an alkyl glucoester, though any suitable naturally derived anionic surfactant may be used. The anionic surfactant provides enhanced hard water tolerance, foam stability, and improved mildness to skin.

The nonionic surfactant component may be a single naturally derived surfactant or a combination of multiple nonionic surfactants. The preferred nonionic surfactant is an alkyl polyglucoside, less preferably a sorbitan ester, though any suitable naturally derived nonionic surfactant may be used. The nonionic surfactant provides effective surface tension reduction, a low critical micelle concentration, and detergency.

Naturally derived surfactants, such as those used in the present invention, are susceptible to "in-can" degradation and consequently are often used in other formulations with synthetic preservatives such as glutaraldehyde and isothiazalone to prevent such degradation. In addition to solubilizing hard water salts, the organic acid, preferably lactic acid, in the present formulation preserves the naturally derived surfactants thus eliminating the need for additional synthetic preservatives. This preservative character of lactic acid is helpful to the present invention because it enables a cleaner formulation devoid of synthetic components that might contribute to skin irritation.

The alkyl polyglucoside component with an average chain length of C12–C16 was found to exhibit excellent detergency and streak-free rinsing on dilution; it is also useful in reducing the critical micelle concentration. The alkyl polyglucoside with an alkyl chain length of C8–C10 was found to hydrotrope or couple in the anionic alkyl glucoester and the C12–C16 alkyl polyglucoside, which exhibited moderate solubilization or hazing. Without the C8–C10 alkyl polyglucoside surfactant, the solution exhibited poor stability at high temperatures.

Naturally derived alkyl glucoesters are extremely mild to the skin compared to traditional anionic surfactants, and can reduce irritancy of other components in the formulation. In addition, the anionic surfactant improves the hard water tolerance of the alkyl polyglucosides.

Optionally, a naturally derived protein, preferably a collagen protein, may be added to the cleaning formulation to provide emolliency and enhance softness to the skin. Naturally derived collagen proteins reduce skin irritancy because they are extremely absorptive to both skin and hair, and thus form a protective barrier against irritation. The preferred invented formulations are free or substantially free of non-naturally-derived or synthetic components. They have no or no significant quantities of or no intentionally added quantities of non-naturally-derived or synthetic components.

Cleaning formulations according to the present invention have been developed for both kitchen and bathroom use, and glass and surface use. The relative concentrations of the components have been optimized for each application to meet its unique demands. The preferred relative concentrations of the individual components are provided for each application in tables 1 and 2 below. A detailed description of the preferred species for each component follows. All values in tables 1 and 2 are weight percents.

TABLE 1

Glass and Multi-Surface Cleaner (Ready-to-Use)

| | Preferred | Less Preferred | Even Less Preferred |
|---|---|---|---|
| 1. Organic Acid | 0.22 | 0.026–18<br>0.044–8.8<br>0.088–2.6 | 0.004–28<br>0.0088–22 |
| 2. Nonionic Surfactant | 0.14 | 0.021–14<br>0.035–7<br>0.07–2.1 | 0.0035–21<br>0.007–17 |
| 4. Anionic Surfactant | 0.01 | 0.0024–1.2<br>0.003–0.3<br>0.006–0.03 | 0.0003–6<br>0.0015–2.1 |
| 5. Protein | 0.005 | 0.0005–0.3<br>0.001–0.1<br>0.0025–0.075 | 0–0.5<br>0.00005–0.25 |
| 6. Water | 99.63 | Balance | Balance |

TABLE 2

All Purpose Cleaner (Ready-to-Use/Dilutable)

| | Preferred | Less Preferred | Even Less Preferred |
|---|---|---|---|
| 1. Organic Acid | 5.3 | 1.8–14<br>2.6–11<br>4.4–7 | 0.088–28<br>0.88–17.6 |
| 2. Nonionic Surfactant | 2.5 | 0.7–12<br>1.4–7<br>2–4.6 | 0.06–36<br>0.12–24 |
| 3. Anionic Surfactant | 0.75 | 0.03–1.5<br>0.3–1.1<br>0.6–0.9 | 0.003–7<br>0.015–3 |
| 4. Protein | 0.05 | 0.0005–0.3<br>0.005–0.1<br>0.02–0.075 | 0–0.5<br>0.00005–0.5 |
| 5. Water | 91.4 | Balance | Balance |

The following description pertains to the most preferable species and form (source) for each of the constituent components listed in tables 1 and 2 above. Unless otherwise indicated, the most preferable form of a particular constituent is the same for both the All Purpose, and Glass and Multi-Surface Cleaner formulations.

The organic acid is most preferably lactic acid. The most preferable source for lactic acid is Purac 88HS from Purac America, Inc. Purac 88HS is an approximately 88% active lactic acid solution with the balance being water. It should be noted that, for example in the All Purpose formulation above, lactic acid most preferably comprises 5.3 wt. % of the total composition, meaning that 6.02 wt. % of Purac 88HS (which is only 88 wt. % active lactic acid) is required to achieve the same 5.3 wt. % lactic acid in the All Purpose formulation. The relative concentration of all remaining components from their respective most preferred sources must be similarly accounted for when computing the required total weight percent of a particular component source, or when substituting other, less preferred sources for the components. For example, a 45 wt. % active malic acid solution must comprise 11.78 wt. % of the All Purpose formulation to achieve the same 5.3 wt. % active organic acid.

The nonionic surfactant is most preferably an alkyl polyglucoside. With respect to the Glass and Multipurpose Cleaner, the alkyl polyglucoside surfactant preferably has a chain length in the range of C8–C10. With respect to the All Purpose, the alkyl polyglucoside surfactant is preferably a combination of two alkyl polyglucoside surfactants having chain lengths in the ranges of C8–C10 and C12–C16 respectively. Preferably, the C8–C10 and C12–C16 alkyl polyglucoside surfactants are present in the All Purpose formulation in the proportions listed in table 3 below. All values in table 3 are weight percents.

TABLE 3

Preferred Concentrations of C8–C10 and C12–C16 Alkyl Polyglucoside Nonionic Surfactants in All Purpose Cleaner

| | Preferred | Less Preferred | Even Less Preferred |
|---|---|---|---|
| 1. C8–C10 | 1.24 | 0.35–7<br>0.7–3.5<br>1–2.1 | 0.035–21<br>0.07–14 |
| 2. C12–C16 | 1.24 | 0.35–5<br>0.75–3.5<br>0.9–2.5 | 0.025–15<br>0.05–10 |

Glucopon 600 from Henkel is the preferred source for C12–C16 nonionic surfactant, and is 50 wt. % active C12–C16 alkyl polyglucoside with the balance being water. Less preferably Glucopon 625, less preferably other alkyl polyglucosides, less preferably other naturally derived nonionic surfactants, may be used. Glucopon 220UP from Henkel is the preferred source for C8–C10 nonionic surfactant, and is 70 wt. % active C8–C10 alkyl polyglucoside with the balance being water. Less preferably, Glucopon 220 or Glucopon 225, less preferably other alkyl polyglucosides, less preferably other naturally derived nonionic surfactants may be used.

The anionic surfactant is preferably an alkyl glucoester; the alkyl group of alkyl glucoesters can have chain lengths such as $C_6$–$C_{22}$. Eucarol AGE-EC is the most preferred source for alkyl glucoester anionic surfactant, and is 30 wt. % active disodium cocopolyglucose citrate alkyl glucoester with the balance being water. It is available from Pilot Chemical Company. It has been surprisingly effective in enhancing foam level and stability of the invented cleaners in the presence of tap water id water). Less preferably Eucarol AGE-ET, less prefereably other alkyl glucoesters such as sodium cocopolyglucose tartrate and disodium cocopolyglucose sulfosuccinate, less preferably other naturally derived anionic surfactants, may be used.

The protein is preferably a collagen protein. Lexein X-250 from Inolex is the most preferred source for collagen protein, and is 50% active hydrolyzed collagen protein. The protein is an optional component, though preferably comprises 0.005 wt. % and 0.05 wt. % of the Glass and Multi-Surface, and All Purpose Cleaners respectively, in order to reduce skin irritancy as hereinbefore described. Less preferably Lexein X-300, less preferably other naturally derived proteins, may be used.

Optionally, a naturally derived organic solvent may be added to the Glass and Multi-Surface Cleaner formulation. The most preferable organic solvent is 100% ethanol. Other organic solvents which may be used include Purasolv EL from Purac America, Inc., ethyl lactate, amyl acetate, or other naturally derived organic esters and solvents. The organic solvent may optionally comprise a combination of at least two naturally derived organic solvents. An organic solvent may be added to the Glass and Multi-Surface Cleaner formulation to aid salvation of a particularly heavy greasy film or residue on a surface. Preferably, an organic solvent would comprise 0–25, more preferably 0.0001–23, more preferably 0.01–20, more preferably 0.1–10, more preferably 1–5, more preferably about 3, wt. % of the total formulation. The remaining active components would remain at their above-stated weight percents with the weight percent of water being reduced accordingly to accommodate the addition of the organic solvent.

As can be seen with respect the All Purpose Cleaner formulation above, the preferred C12–C16 alkyl polyglucoside and the preferred C8–C10 alkyl polyglucoside are present in approximately equal amounts of their active components (about 1.24 wt. % each). Thus, the ratio of one to the other is preferably 10:10. This ratio less preferably can vary from 0:10 to 1:10 to 3:10 to 5:10 to 7:10 to 9:10 to 10:9 to 10:7 to 10:5 to 10:3 to 10:1 to 10:0.

The All Purpose Cleaner is preferably provided in a bottle with a twist cap. It can be used full strength or diluted with water to about or at least ¾, ½, ¼, ⅛, 1/10, 1/15, 1/20, 1/30, 1/40, 1/80, 1/160 or 1/320 strength.

The Glass and Multi-Surface Cleaner preferably is provided in a spray bottle. The invented composition preferably has a pH of 2.5–12.5, more preferably 2.5–6 or 8–12, more preferably 3–5 or 9–11.5, more preferably 3.5–4.5 or 11–11.5, preferably adjusted with caustic soda.

In addition to the components described above, one may add naturally derived solvents, humectants (such as glycerin), thickeners, fragrances, etc., to achieve desired performance and aesthetic characteristics.

The formulations are prepared or blended using customary and known methods, the temperature preferably being ambient. The product is used as per conventional methods, typically for floors, windows, hard surfaces, sinks, chrome, plumbing fixtures, shower doors, showers, bathtubs, plastic surfaces, counter tops, tables, furniture, cupboards, glass surfaces, and Formica surfaces.

Tests have been conducted to determine the toxicity and degradability of cleaning formulations according to the present invention. The invented cleaning formulations have exhibited less than 0.05% volatile organic compound (VOC) content compared It with up to 10% VOC for conventional synthetic cleaners. VOCs evaporate and pollute (contaminate) indoor air contributing to "sick building" syndrome which is known to aggravate certain types of pulmonary conditions such as asthma. In addition, the invented cleaners exhibited a dermal toxicity (LD 50) of greater than 2000 mg/kg, which is considered to be non-irritating. Oral toxicity for the invented cleaners was also extremely low at 12,526 mg/kg.

The invented all naturally derived cleaners were found to exhibit rapid environmental degradation and biodegradation compared to conventional synthetic cleaners. The invented cleaners degrade in the environment 58% in 5 days, 83% in 15 days, and 100% in 28 days, representing a significant improvement in degree and rapidity of environmental degradation compared with conventional synthetic cleaners. It is the current standard to consider a product "readily biodegradable" if it degrades 60% in 28 days.

The invented cleaners further exhibited anaerobic degradation of 84.5% in 6 days. Anaerobic degradation of at least 60% in 56 days is considered acceptable by ASTM standard test methods for determining the Anaerobic Biodegradation of Organic Chemicals, Test Method 1196–92. A high rate of anaerobic biodegradation indicates the potential for high biodegradability in private septic systems, waste treatment plants, anaerobic digesters, and in many naturally anaerobic environments such as river and lake sediments.

Although the hereinabove described embodiments of the invention constitute the preferred embodiments, it should be understood that modifications can be made thereto without departing from the scope of the invention as set forth in the appended claims.

What is claimed is:

1. A cleaning composition comprising 0.004–28 weight percent naturally derived organic acid, 0.0035–36 weight percent naturally derived alkyl polyglucoside nonionic surfactant, and 0.0003–7 weight percent naturally derived alkyl glucoester anionic surfactant, said cleaning composition being an aqueous solution, wherein the alkyl group of said alkyl glucoester has a chain length of $C_6$–$C_{22}$.

2. A cleaning composition according to claim 1, wherein said organic acid is a C2–C6 organic acid.

3. A cleaning composition according to claim 1, wherein said organic acid is lactic acid.

4. A cleaning composition according to claim 1, wherein said nonionic surfactant comprises an alkyl polyglucoside having a chain length in the range of C8–C10.

5. A cleaning composition according to claim 4, said nonionic surfactant further comprising an alkyl polyglucoside having a chain length in the range of C12–C16.

6. A cleaning composition according to claim 1, wherein said alkyl glucoester anionic surfactant is sodium cocopolyglucose tartrate.

7. A cleaning composition according to claim 1, wherein said alkyl glucoester anionic surfactant is disodium cocopolyglucose citrate.

8. A cleaning composition according to claim 1, further comprising 0.00005–0.5 weight percent naturally derived protein.

9. A cleaning composition according to claim 8, wherein said protein is a collagen protein.

10. A cleaning composition according to claim 1, further comprising 0.0001–25 weight percent naturally derived organic solvent.

11. A cleaning composition according to claim 10, wherein said organic solvent is selected from the group consisting of ethanol, ethyl lactate, amyl acetate and mixtures thereof.

12. A cleaning composition according to claim 1, wherein said cleaning composition has a pH in the range of 2.5–6.

13. A cleaning composition according to claim 1, wherein said cleaning composition has a pH in the range of 3–5 or 9–11.5.

14. A cleaning composition according to claim 3, further comprising 0.00005–0.5 weight percent naturally derived protein.

15. A cleaning composition according to claim 1, wherein said cleaning composition consists essentially of said organic acid, said alkyl polyglucoside nonionic surfactant, and said alkyl glucoester anionic surfactant.

16. A cleaning composition according to claim 15, wherein said organic acid is a C2–C6 organic acid.

17. A cleaning composition according to claim 15, wherein said organic acid is lactic acid.

18. A cleaning composition according to claim 15, wherein said nonionic surfactant comprises an alkyl polyglucoside having a chain length in the range of C8–C10.

19. A cleaning composition according to claim 16, wherein said nonionic surfactant comprises an alkyl polyglucoside having a chain length in the range of C8–C10.

20. A cleaning composition according to claim 19, wherein said alkyl glucoester is disodium cocopolyglucose citrate.

21. A method of cleaning a substrate comprising the steps of applying to said substrate a cleaning composition and thereafter cleaning said substrate utilizing said composition, said composition comprising 0.004–28 weight percent naturally derived organic acid, 0.0035–36 weight percent naturally derived alkyl polyglucoside nonionic surfactant, and 0.0003–7 weight percent naturally derived alkyl glucoester anionic surfactant, said cleaning composition being an aqueous solution, wherein the alkyl group of said alkyl glucoester has a chain length of $C_6$–$C_2$.

22. A method according to claim 21, wherein said organic acid is a C2–C6 organic acid.

23. A method according to claim 21, wherein said organic acid is lactic acid.

24. A method according to claim 21, wherein said alkyl glucoester anionic surfactant is disodium cocopolyglucose citrate.

25. A method according to claim 21, wherein said nonionic surfactant comprises an alkyl polyglucoside having a chain length in the range of C8–C10.

26. A method according to claim 22, wherein said nonionic surfactant comprises an alkyl polyglucoside having a chain length in the range of C8–C10.

27. A method according to claim 26, wherein said alkyl glucoester is disodium cocopolyglucose citrate.

28. A method according to claim 21, wherein said composition further comprises 0.00005–0.5 weight percent naturally derived protein.

29. A method according to claim 28, wherein said protein is collagen protein.

30. A method according to claim 28, wherein said cleaning composition consists essentially of said organic acid, said nonionic surfactant, and said anionic surfactant.

31. A method according to claim 30, wherein said organic acid is a C2–C6 organic acid.

32. A method according to claim 30, wherein said organic acid is lactic acid.

33. A method according to claim 30, wherein said nonionic surfactant comprises an alkyl polyglucoside having a chain length in the range of C8–C10.

34. A method according to claim 31, wherein said nonionic surfactant comprises an alkyl polyglucoside having a chain length in the range of C8–C10.

35. A method according to claim 34, wherein said alkyl glucoester is disodium cocopolyglucose citrate.

36. The cleaning composition of claim 1, wherein all cleaning components in said cleaning composition are naturally derived.

37. The cleaning composition of claim 1, wherein all components in said cleaning composition are naturally derived.

38. The cleaning composition of claim 7, wherein said organic acid is lactic acid.

39. The method of claim 21, wherein all cleaning components in said cleaning composition are naturally derived.

40. The method of claim 21, wherein all components in said cleaning composition are naturally derived.

41. The method of claim 23, wherein said alkyl glucoester is disodium cocopolyglucose citrate.

42. The method of claim 21, wherein said substrate is a hard surface substrate.

43. The method of claim 21, wherein said substrate is a hard surface in a kitchen or bathroom.

44. The method of claim 21, wherein said substrate is selected from the group consisting of floors, windows, hard surfaces, metal, sinks, chrome, plumbing fixtures, shower doors, showers, bathtubs, plastic surfaces, counter tops, tables, furniture, cupboards and glass surfaces.

45. The method of claim 21, wherein said cleaning composition is selected from the group consisting of dishwashing, laundry and carpet cleaners.

* * * * *

UNITED STATES PATENT AND TRADEMARK OFFICE
CERTIFICATE OF CORRECTION

PATENT NO.    : 6,432,395 B1                                              Page 1 of 1
DATED         : August 13, 2002
INVENTOR(S)   : Rochon et al.

It is certified that error appears in the above-identified patent and that said Letters Patent is hereby corrected as shown below:

Column 2,
Line 3, please delete "surfactant" and insert therefor -- surfactants --.

Column 4,
Line 57, please delete "id" and insert therefor -- (hard --.

Column 5,
Line 13, please delete "salvation" and insert therefor -- solvation --.
Line 55, please delete "It".

Column 7,
Line 23, please delete "$C_2$" and insert therefor -- $C_{22}$ --.

Column 8,
Line 1, please delete "28," and insert therefor -- 21, --.

Signed and Sealed this

Seventeenth Day of December, 2002

JAMES E. ROGAN
*Director of the United States Patent and Trademark Office*